United States Patent [19]

Segers

[11] Patent Number: Plant 7,281

[45] Date of Patent: Jul. 24, 1990

[54] SARDIS

[75] Inventor: Th. A. Segers, Hoofddorp, Netherlands

[73] Assignee: Twyford Plant Laboratories, Inc., Santa Paula, Calif.

[21] Appl. No.: 316,908

[22] Filed: Feb. 28, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Townsend and Townsend

[57] ABSTRACT

An original variety of gerbera plant distinguished by a red color of its flowers, and its ability to grow vigorously and flower profusely during the spring, midseason, and fall blooming periods as well as blooming in the winter in the greenhouse.

2 Drawing Sheets

BACKGROUND OF THE PLANT

This gerbera variety, named 'Sardis', originated as a seedling at Rijsenhout, and resulted from the crossing in March of 1981 of 78-817 as the seed parent and the pollen parent identified as 77-224, taken from my collection of gerbera maintained for breeding purposes at Rysenhout, the Netherlands. My objective in making the crossing being to develop new gerbera varieties having blooms of good quality and excellent color on strong plants having good winter production in my greenhouses. This plant was selected from the seedlings resulting from the above crossing because of its big semi-double flower having a particularly intensely red flower coloration, and its vigorous and strong growth habit. The characteristics embracing the above objectives along with other desirable improvements as set forth below distinguish this new plant from its parents as well as from all other varieties of which I am aware.

The varieties thought to be most similar are 'Vesta', 'Marleen' and 'Atlas'. 'Sardis' is distinguished from 'Vesta' by its better color, semi-double, and stronger flower stem. 'Sardis' is distinguished from 'Marleen' by its different floral color, and semi-double, bigger flower. 'Sardis' is distinguished from 'Atlas' by its more intensive color, and semi-double, bigger flower.

Asexual propagation of this selected plant was carried on under my direction at Rysenhout by cuttings and further by means of tissue culture at Naaldwijk, the Netherlands, through several successive generations which clearly demonstrated that the novel characteristics of its blooming and growth habits appear to be firmly fixed and would remain true from generation to generation.

The following is a detailed description of my new gerbera plant based upon observations of greenhouse plants grown at Naaldwijk, Netherlands, the color designations being according to The R.H.S. Colour Chart published by The Royal Horticultural Society of London, England.

DESCRIPTION OF THE DRAWING

This new variety is illustated by the accompanying photographic drawing (FIG. 1.) which shows its bloom in full color, with such colors of the photographic being as true to those of the plant as can be reasonably obtained from conventional professional photographic procedures.

DESCRIPTION OF THE PLANT

Leaf length: Long.
Leaf width: Medium.
Leaf blade thickness: Medium.
Leaf blade blistering: Weak.
Leaf blade pubescence on upper side mid-rib excluded: Medium.
Leaf blade depth of incisions o nbasal part: Deep.
Leaf blade depth ofincisions on the central third: Medium.
Leaf blade depth of incisions on distal part: Shallow.
Leaf blade color or upper side: Medium Green RHS 137 A.
Leaf blade glossiness of upper side: Medium.
Leaf blade angle of apex: Obtuse.
Leaf blade shape of apex: Pointed.
Leaf blade margin of lobes: Dentate, to undulated.
Leaf blade extensions of margin: Medium.
Petiole length: Medium.
Petiole anthocyanin coloration: Present.
Petiole intensity of anthocyanin coloration: Weak.

DESCRIPTION OF THE FLOWER

Peduncle length: Medium.
Peduncle cross section:
*Elliptic.*—to round.
Peduncle tendency to fasciation: Present.
Peduncle thickness;: medium.
Peduncle strength: Strong.
Peduncle pubescence: Medium.
Peduncle color: Medium Green RHS 144 C.
Peduncle anthocyanin color at base: Present.
Peduncle intensity of anthocyanin coloration at base: Very weak.
Peduncle anthocyanin coloration at top: Present, unilateral.
Peduncle involucral bracts: Present.
Flower head type: Semi-Double.
Flower head diameter: Medium.
Flower head height from point of attachment of involucre to top flower head: Medium.
Flower head height of involucre: Medium.
Flower head diameter of involucre: Medium.
Flower head number of involucral bracts: Medium.
Flower head longitudinal axis of bracts of inner rows of involucre: Reflexing.

Flower head anthocyanin coloration at top of inner involucral bracts: Absent.
Flower head intensity of anthocyanin coloration at top of inner involucral bracts: 0
Flower head pubescence of involucre: Medium to Strong.
Flower head number of ray florets of outer rows: Medium.
Flower head shape of ray florets of out row: Narrow elliptic.
Ray floret longitudinal axis of rays of outer row: Reflexing.
Ray floret longitudinal axis of rays of inner row (normally developed ray florets): Straight to reflexing.
Female floret longitudinal axis of ray (outer ray florets excluded—semi-double or double varieties only): Straight.
Male floret longitudinal axis of ray (semi-double or double varieties only): Straight, top bent upward.
Outer ray floret cross section of ray: Flat.
Outer ray floret length: Long.
Outer ray floret width: Medium.
Outer ray floret longitudinal folding: Medium.
Outer ray floret angle of apex: Acute to right angle.
Outer ray floret shape of apex: Rounded.
Outer ray floret incisions of apex: Present.
Outer ray floret nnumber of incisions: Two.
Outer ray floret depth of incisions: Medium to deep.
Outer ray floret length of free petals: Short.
Outer ray floret color of inner side: RHS 46B, red.
Outer ray floret distribution of the color on the inner side: Uniform.
Outer ray floret edge of different color: Absent.

Outer ray floret striation: Absent.
Outer ray floret color of outer side:

| Description | Remarks |
|---|---|
| RHS 43B | Base red RHS 43B |
| RHS 35B | Toward top somewhat lighter; top with yellowish green tint. |

Outer ray floret claw spot: Present.
Disc diameter (single or semi-double varieties only): Medium.
Disc main color before flowering of disc florets (single or semi-double varieties only): Green RHS 144 A.
Disc main color of perianth lobes of female flowers: RHS 46 B, Red.
Disc main color of perianth lobes of male flowers: Red, dentated white RHS 43 B.

DESCRIPTION OF REPRODUCTION ORGANS

Style main color of distal part: Red RHS 35 D.
Stigma main color: Yellow RHS 2 D.
Anthers main color: Dark Yellow RHS 16 A.
Anthers color of two relative to other parts: Lighter.
Anthers longitudinal stripes: Absent.
Pappus main color: Yellow RHS 144 A.
Pappus color of top relative to other parts: Identical.
Pappus level of top relative to closed disc florets: Same.

I claim:

1. The new distinct variety of gerbera plant herein described and illustrated and identified by the characteristics enumerated above.

* * * * *

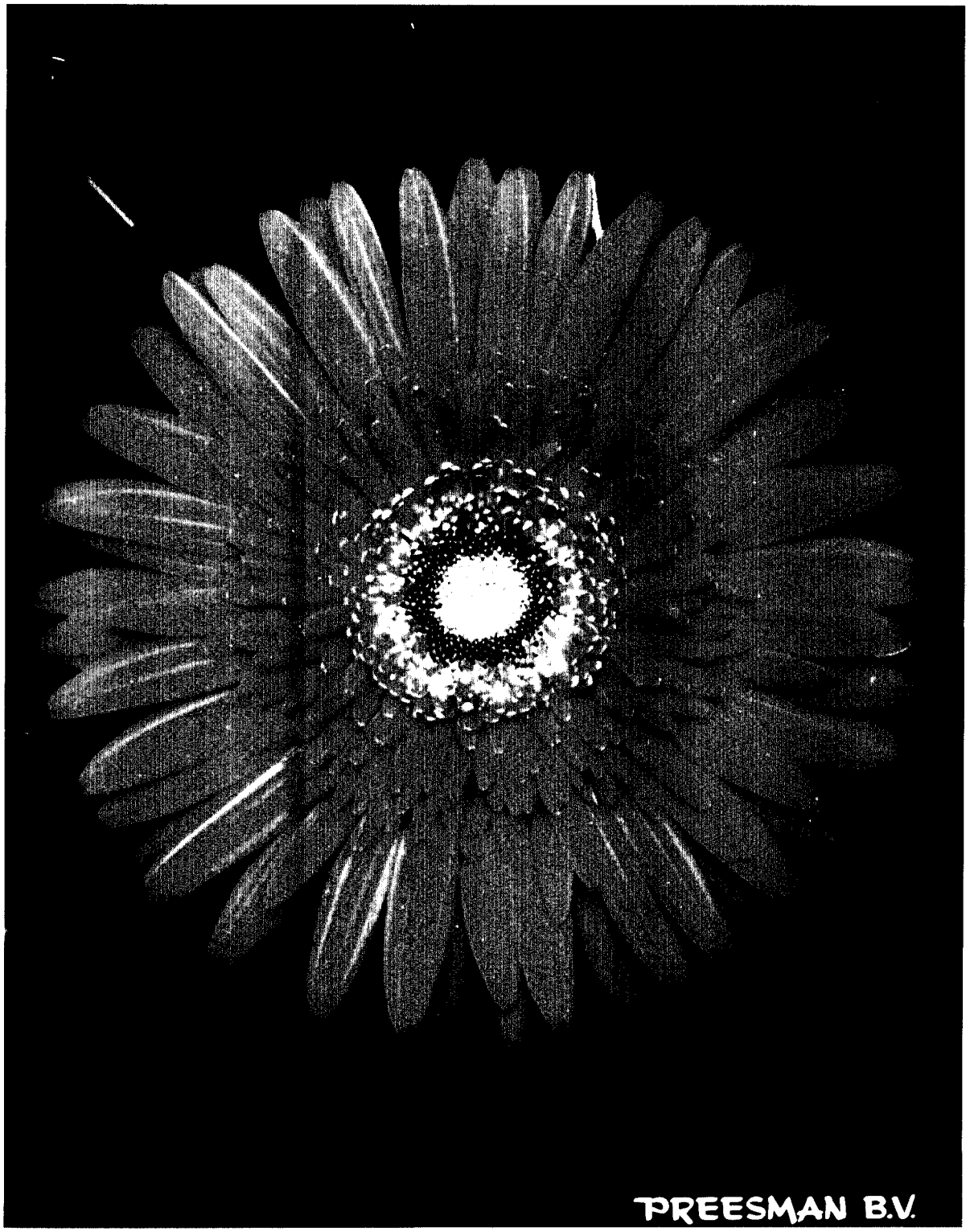
PREESMAN B.V.

UNITED STATES PATENT AND TRADEMARK OFFICE

CERTIFICATE OF CORRECTION

PATENT NO. : Plant 7,281

DATED : July 24, 1990

INVENTOR(S) : Th. A. Segers

It is certified that error appears in the above-identified patent and that said Letters Patent is hereby corrected as shown below:

In column 1, line 45, please delete "colors of the photographic being" and substitute therefor, --colors of the photograph being--;

In column 2, line 10, please delete "incisions o nbasal part" and substitute therefor, --incisions on basal part--;

In column 2, line 11, please delete "depth ofincisions" and substitute therefor, --depth of incisions--;

In column 2, line 44, please delete "to top flower head" and substitute therefor, --to top of flower head--;

In column 3, line 28, please delete "floret nnumber" and substitute therefor, --floret number--; and In column 4, line 24, please delete "color of two" and substitute therefor, --color of top--.

Signed and Sealed this

Twenty-sixth Day of November, 1991

*Attest:*

*Attesting Officer*

HARRY F. MANBECK, JR.

*Commissioner of Patents and Trademarks*